United States Patent [19]

Brois et al.

[11] 4,221,720
[45] Sep. 9, 1980

[54] THIO-BIS ALKYL LACTONE ACIDS AND ESTERS THEREOF

[75] Inventors: Stanley J. Brois, Westfield; Antonio Gutierrez, Hamilton Square, both of N.J.

[73] Assignee: Exxon Research & Engineering Co., Florham Park, N.J.

[21] Appl. No.: 967,289

[22] Filed: Dec. 7, 1978

Related U.S. Application Data

[62] Division of Ser. No. 806,326, Jun. 13, 1977, Pat. No. 4,167,514, which is a division of Ser. No. 726,206, Sep. 24, 1976, Pat. No. 4,062,786.

[51] Int. Cl.$^2$ .................. C07D 307/10; C07D 309/20
[52] U.S. Cl. .............................. 260/343.6; 260/343.5; 260/346.74; 548/237
[58] Field of Search .......................... 260/343.6, 343.5

[56] References Cited

U.S. PATENT DOCUMENTS

| | | | |
|---|---|---|---|
| 3,470,098 | 9/1969 | O'Halloran | 252/47.5 |
| 4,123,373 | 10/1978 | Brois et al. | 260/343.6 |
| 4,142,866 | 3/1979 | Brois et al. | 260/343.6 |
| 4,167,514 | 9/1979 | Brois et al. | 260/343.5 |

Primary Examiner—Henry R. Jiles
Assistant Examiner—Jane T. Fan
Attorney, Agent, or Firm—Frank T. Johmann

[57] ABSTRACT

Lactone oxazoline reaction products of hydrocarbon substituted lactone carboxylic acids, for example, polybutyl lactone carboxylic acid, with 2,2-disubstituted-2-amino-1-alkanols, such as tris-(hydroxymethyl)aminomethane (THAM), and their derivatives are useful aditives in oleaginous compositions, such as sludge dispersants for lubricating oil, or anti-rust agents for gasoline.

12 Claims, No Drawings

THIO-BIS ALKYL LACTONE ACIDS AND ESTERS THEREOF

This is a division of application Ser. No. 806,326, filed June 13, 1977, now U.S. Pat. No. 4,167,514 which was a division of Ser. No. 726,206 filed Sept. 24, 1976 and now U.S. Pat. No. 4,062,786.

BACKGROUND OF THE INVENTION AND PRIOR ART

The present invention concerns hydrocarbon soluble alkyl lactone oxazolines, their method of preparation, the utility of said lactone oxazolines in hydrocarbon fuel and lubricating systems as highly stable anti-rust agents and/or sludge dispersants.

During the past decade, ashless sludge dispersants have become increasingly important, primarily in improving the performance of lubricants and gasoline in keeping the engine clean of deposits, and permitting extended crankcase oil drain periods. Most commercial ashless dispersants fall into several general categories. In one category, an amine or polyamine is attached to a long chain hydrocarbon polymer, usually polyisobutylene, obtained by the reaction of halogenated olefin polymer with polyamine as in U.S. Pat. Nos. 3,275,554; 3,565,592; 3,565,804. In another category, a polyamine is linked to the polyisobutylene through an acid group, such as a long chain monocarboxylic acid, e.g., see U.S. Pat. No. 3,444,170 or a long chain dicarboxylic acid such as polyisobutenylsuffinic anhydride, by forming amide or imide linkages, such as described in U.S. Pat. Nos. 3,172,892; 3,219,666; etc. In still another category the amines and polyamines are linked to the polyalkyl chain through a dicarboxylic acid lactone such as described in U.S. Pat. Nos. 3,200,075; 3,261,782; 3,897,350; 3,936,472, etc.

U.S. Pat. No. 3,261,782 teaches that alkylbutyrolactone-α acetic acids themselves are useful rust inhibitors in lubricating oil compositions which acids are derived from long chain dicarboxylic acids.

Reaction products of hydrocarbon substituted succinic anyhydride, e.g., the aforesaid polyisobutenylsuccinic anhydride, with compounds containing both an amine group and a hydroxy group, have been suggested or investigated in the prior art. For example, U.S. Pat. No. 3,272,746 teaches the reaction of ethanolamine and diethanolamine, as well as various hydroxyalkyl substituted alkylene amines, such as N-(2-hydroxyethyl) ethylene diamine, N,N'-bis(2-hydroxyethyl) ethylene diamine, with alkenyl succinic anhydride to obtain ashless dispersants for lube oil. A hydroxy amine, such as diethanolamine, is reacted with a long chain alkenylsuccinic anhydride in U.S. Pat. No. 3,324,033 to form a mixture of esters and amides, wherein some of the diethanolamine reacts through a hydroxy group to give an ester linkage, while another portion of the diethanolamine forms an amide linkage.

United Kingdom Specification No. 809,001 teaches corrosion inhibitors comprising a multiple salt complex derived from the reaction product of hydrocarbyl substituted dicarboxylic acids and hydroxy amines (including 2-amino-2-methyl-1,3-propanediol [AMPD]) and tris-hyroxymethylaminomethane (THAM) further complexed with mono- and polycarboxylic acids (see Examples 17-19).

U.S. Pat. No. 3,576,743 teaches reacting polyisobutenylsuccinic anhydride with a polyol, such as pentaerythritol, followed by reaction with THAM, (see Example 1). U.S. Pat. No. 3,632,511 teaches reacting polyisobutenylsuccinic anhydride with both a polyamine and a polyhydric alcohol including THAM. U.S. Pat. No. 3,697,428 (Example 11) teaches reacting polyisobutenylsuccinic anhydride with a mixture of pentaerythritol and THAM. United Kingdom Specification No. 984,409 teaches ashless, amide/imide/ester type lubricant additives prepared by reacting an alkenyl succinic anhydride, said alkenyl group having 30 to 700 carbon atoms, with a hydroxy amine including THAM.

DOS No. 2512201 teaches reacting long chain hydrocarbon substituted succinic anhydride with 2,2'-disubstituted-2-amino-1-alkanol to produce mono- and bis-oxazoline products (see also DOS No. 2534921/2 for similar reaction products which can also be modified by reaction with phosphorus, boron or oxygen compounds).

The earlier referenced category of dicarboxylic acid lactone type products have also been provided with anti-rust and/or dispersant properties by reaction with hydroxy amines such as ethanolamine and diethanolamine (see U.S. Pat. Nos. 3,248,187 and 3,620,977).

SUMMARY OF THE INVENTION

As noted above, the prior art teaches oil-soluble additives formed from hydrocarbyl substituted dicarboxylic acid material which has been converted into a lactone and reacted with various amino or hydroxy compounds either through an amide, imide or ester linkage, and that these additives are stated to be useful for various functions, such as anti-rust agents, detergents, or dispersants for oleaginous compositions including lube oil, gasoline, turbine oil and oils for drilling applications.

It has now been discovered that long chain hydrocarbon structures which feature vicinal lactone and oxazoline ring systems can be so constructed using novel synthetic methods whereby a highly stable additive of enhanced dispersancy, enhanced viscosity properties, and/or anti-rust properties is obtained. Moreover, further functionalization of this dual heterocyclic system via our new processes with vicinal hydroxyl, thiyl and sulfo groups can engender other desirable properties, such as anti-oxidation and anti-corrosion activity. This novel class of additives can be represented in part by the formula:

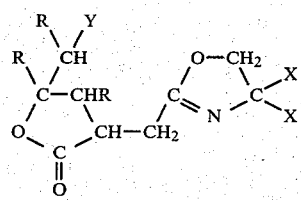

wherein R is selected from the group consisting of hydrogen and alkyl radicals containing from 1 to 400 or more carbons, X is selected from the group consisting of an alkyl or hydroxy alkyl group and at least one of the X substituents and preferably both of the X substituents being a hydroxy alkyl group of the structure —(CH$_2$)$_n$OH where n is 1 to 3 and Y is selected from the group consisting of hydrogen, hydroxyl, sulfo, alkylthio (TS—), alkyldithio (TSS—), and a sulfur bridge, e.g., —S— and —S—S—, joining two lactone oxazoline units together as depicted below wherein z is a number ranging from 1 to 4 and T is defined hereafter as containing 1 to 50, preferably 2 to 20 carbons.

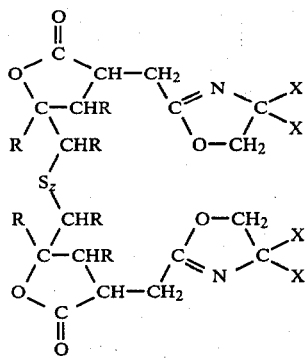

Preferred herein is polyisobutyl lactone oxazoline of number average molecular weight ranging from about 400 to 100,000 prepared by the reaction of equimolar proportions of polyisobutyl lactone carboxylic acid with tris-[hydroxymethyl] aminomethane at a temperature from about 100°–240° C. preferably 150°–180° C. until two moles of H₂O per mole of reactant is removed from the reaction.

The novel compounds described above as effective detergents in lubricating oil compositions are also useful as detergents in fuel compositions, such as burner fuel compositions, and motor fuel compositions, for example, in gasolines and in diesel fuels. Thus, it is within the scope of this invention to dissolve a small but at least an effective amount of said compounds of the invention in a major proportion of an oleaginous material to provide useful oleaginous compositions.

These hydrocarbon soluble compounds have at least 8 carbons in the substantially saturated aliphatic hydrocarbyl group and a carboxylic acid group of the dicarboxylic acid material converted into a lactone ring and another carboxylic acid group converted into an oxazoline ring as a result of the reaction of at least equimolar amounts of said hydrocarbon substituted dicarboxylic acid lactone material and a 2,2-disubstituted-2-amino-1-alkanol having 1 to 3 hydroxy groups and containing a total of 4 to 8 carbons.

These novel alkyl lactone oxazolines of the present invention can be prepared as noted by heating together alkyl lactone acids, esters or amides with a 2,2-disubstituted-2-amino-1-alcohol, such as tris-(hydroxylmethyl) aminomethane, as expressed in the following equation:

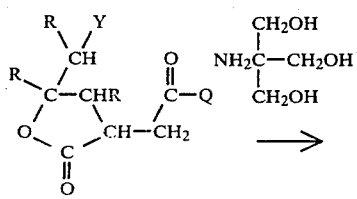

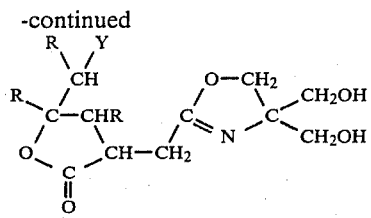

wherein R is as previously defined and Q is as subsequently defined.

ALKYL LACTONE REACTANTS

The preparation of the requisite reactants involves a lactonization of an alkenyl succinic acid analog obtained via the Ene reaction of an olefin with an alpha-beta unsaturated C₄ to C₁₀ dicarboxylic acid, or anhydrides or esters thereof, such as fumaric acid, itaconic acid, maleic acid, maleic anhydride, dimethyl fumarate, etc. The dicarboxylic acid material can be illustrated by an alkenyl substituted anhydride which may contain a single alkenyl radical or a mixture of alkenyl radicals variously bonded to the cyclic succinic anhydride group, and is understood to comprise such structures as:

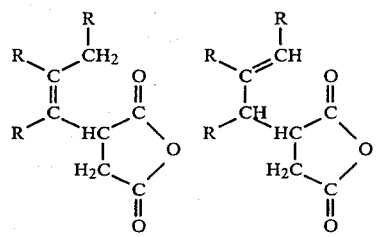

wherein R may be hydrogen or hydrocarbyl or substituted hydrocarbyl each having from 1 to about 400 and more carbons, and preferably from 1 to about 200 carbon atoms. The anhydrides can be obtained by well-known methods, such as the reaction between an olefin and maleic anhydride or halosuccinic anhydride or succinic ester (U.S. Pat. No. 2,568,876). In branched olefins, particularly branched polyolefins, R may be hydrogen, methyl or a long chain hydrocarbyl group. However, the extact structure may not always be ascertained and the various R groups cannot always be precisely defined in the Ene products from polyolefins and maleic anhydride.

Suitable olefins include butene, isobutene, pentene, decene, dodecene, tetradecene, hexadecene, octadecene, eicosene, and polymers of propylene, butene, isobutene, pentene, decene and the like, and halogen-containing olefins. The olefins may also contain cycloalkyl and aromatic groups. The most preferred alkenyl succinic anhydrides used in this invention are those in which the alkenyl group contains a total of from 4 to 400 carbon atoms; from 4 to about 20 carbon atoms for aqueous systems; and at least 8 to 400 and more preferably 10 to 300 for hydrocarbon systems.

Many of these hydrocarbyl substituted dicarboxylic acid materials and their preparation are well known in the art as well as being commercially available, e.g., 2-octadecenyl succinic anhydride and polyisobutenyl succinic anhydride.

With 2-chloromaleic anhydride and related acylating agents, alkenylmaleic anhydride reactants are formed.

Lactonization of these products also afford useful precursors to lactone oxazoline products.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; butylene and isobutylene; propylene and isobutylene; etc. Other copolymers include those in which a minor molar amount of the copolymer monomers, e.g., 1 to 20 mole % is a $C_4$ to $C_{18}$ non-conjugated diolefin, e.g., a copolymer of isobutylene and butadiene; or a copolymer of ethylene, propylene, and 1,4-hexadiene; etc.

The olefin polymers will usually have number average molecular weights within the range of about 750 and about 200,000, more usually between about 1000 and about 20,000. Particularly useful olefin polymers have number average molecular weights within the range of about 900 and about 3000 with approximately one terminal double bond per polymer chain. An especially valuable starting material for a highly potent dispersant additive are polyalkenes e.g. polyisobutylene, having up to 10,000 carbons.

Especially useful when it is desired that the dispersant additives also possess viscosity index improving properties are 5,000 to 200,000, e.g., 25,000 to 100,000 number average molecular weight polymers. An especially preferred example of such a V.I. improving polymer is a copolymer of about 30 to 85 mole % ethylene, about 15 to 70 mole % $C_3$ to $C_5$ mono-alpha-olefin, preferably propylene, and 0 to 20 mole % of a $C_4$ to $C_{14}$ non-conjugated diene.

These ethylene-propylene V.I. improving copolymers or terpolymers are usually prepared by Ziegler-Natta synthesis methods, e.g., see U.S. Pat. No. 3,551,336. Some of these copolymers and terpolymers are commercially available, such as VISTALON ®, an elastomeric terpolymer of ethylene, propylene and 5-ethylidene norbornene, marketed by Exxon Chemical Co., New York, N.Y. and NORDEL ®, a terpolymer of ethylene, propylene and 1,4-hexadiene marketed by E. I. duPont de Nemours & Co.

Unsubstituted or simple lactone reactants (Y=H) are readily obtained by the acid-catalyzed lactonization of an alkenyl dicarboxylic acid analog, the latter being derived from the ring scission of an alkenyl succinic anhydride with water, an alcohol or an amine as shown below wherein HQ represents water, alcohols containing from 1 to 10 carbons and dialkyl amines containing from 2 to 10 carbons and R is as previously defined.

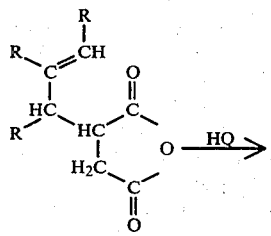

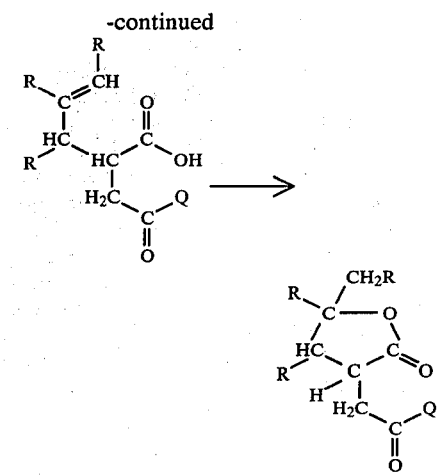

The reaction with HQ is assumed to open the anhydride at the least congested carbonyl group and form a succinic acid, hemi-ester or amic acid product which in the presence of an acid catalyst cyclizes mostly to the 5-ring lactone product as shown above.

It is possible to use alkenyl substituents with the double bond in the 1, 2, or 3-position or even double bonds further out on the hydrocarbyl chain since the acid catalyst is capable at moving it into a position suitable for lactone formation. In general, the size of the lactone ring formed will depend upon, inter alia, the position of the double bond, and which carboxylic acid group participates in the lactone forming reaction. As a consequence, both 5- and 6-ring (or larger ring) lactones can be envisaged as illustrated below:

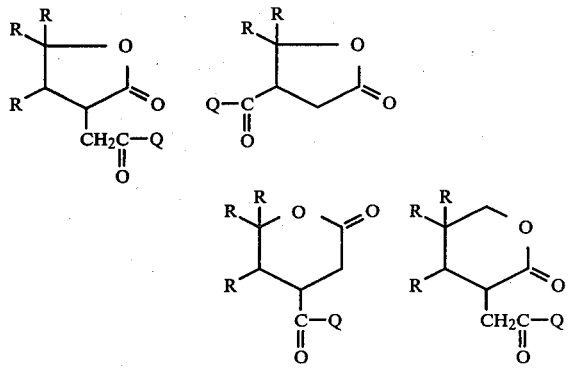

For convenience, the products of the present invention are usually shown as 5-ring lactones although larger ring lactone products can also be present.

LACTONIZATION CATALYSTS

The intramolecular cyclization step involved in the process of this invention must be carried out in the presence of an acid-type catalyst in order to effect formation of the lactone. Suitable catalysts include the mineral acids such as hydrochloric acid, sulfuric acid, perchloric acid, and phosphoric acid; the sulfonic acids such as the alkanesulfonic acids and the arylsulfonic acids; the Lewis type acids such as aluminum chloride, boron trifluoride, antimony trichloride, and titanium tetrachloride; low molecular weight sulfonic acid type ion exchange resin materials, such as cross-linked sulfonated polystyrene which is commercially available as Dowex-50. The alkanesulfonic acid catalysts are preferably the lower alkanesulfonic acids containing from 1 to 12 carbon atoms, for example, methanesulfonic acid, ethanesulfonic acid, propanesulfonic acid, and butanesulfonic acid. If desired, a mixture of lower alkanesulfonic acids can be used and such a mixture containing methane, ethane, and propanesulfonic acids is commercially available. Ordinarily, the alkanesulfonic acid will comprise from 92% to 95% sulfonic acid, from 1 to 2% sulfuric acid, and from 3 to 6% water. The arylsulfonic acid catalyst which can be used in the process includes the benzenesulfonic acids, toluenesulfonic acid, and chlorobenzenesulfonic acids, with p-toluenesulfonic acid and 4-chloro-benzenesulfonic acid being preferred. The amount of catalyst present in the reaction zone can be varied over wide limits depending upon the nature of the reactants and the catalyst used. The amount of catalyst used is also determined to a considerable extent by the temperature selected for conducting the reaction. Thus, at higher temperatures the amount of catalyst required in the reaction is less than when lower temperatures are used and the use of excessive amounts of catalyst at the more elevated temperatures will promote the formation of undesired side products. Ordinarily, the amount of catalyst used will be between about 0.1% up to 10% by weight of the amount of the alkenyl succinic anhydride reactant.

SUBSTITUTED LACTONE REACTANTS

The presence of certain heteroatoms adjacent to the novel lactone oxazoline ring combination oftimes endows the novel lactone oxazoline system with other desirable properties such as antioxidation and anticorrosion activity. In the present invention, we have devised novel ways of introducing hydroxyl, thiyl, sulfide, sulfoxide, sulfone and sulfo groups adjacent to the lactone oxazoline functions as described below:

HYDROXYL LACTONE AND EPOXY REACTANTS

Hydroxyl containing lactone reactants are prepared via the addition of peracids, hydrocarbyl peroxides or aqueous hydrogen peroxide to alkenyl succinic acid, hemiester or amide reagents as shown below:

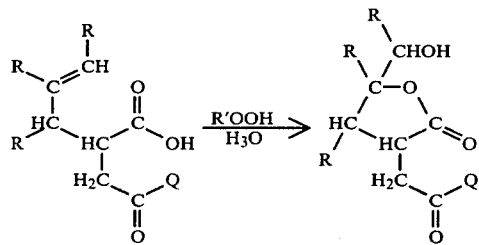

wherein Q is as previously defined and R' represents hydrogen, acyl group containing from 2 to 20 carbons or alkyl group containing from 2 to 20 carbons. As an alternate, the epoxidation of alkenyl succinic anhydride, with peracids gives epoxy anhydrides which can react with (1) water, alcohols or amines to generate the desired hydroxy-substituted lactone reactants or (2) directly with THAM to give the lactone oxazoline end-products.

The thiyl substituted lactones can be conveniently prepared via (1) thiol-induced scission of epoxide anhydrides as shown below wherein T represents alkyl, aryl or heterocyclic groups containing from 1 to 50 carbons

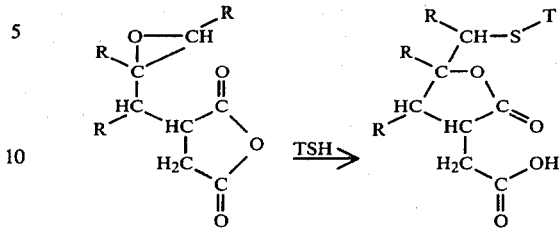

or via (2) sulfenyl halide addition to the double bond in alkenyl succinic acids or esters followed by lactonization via an internal displacement of halide as shown below:

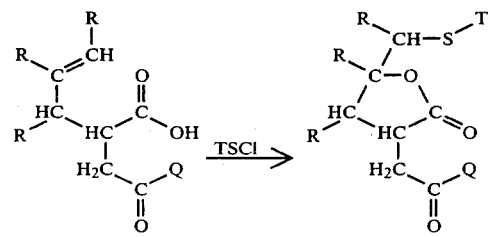

wherein T is defined as above.

The type of thiyl substituted lactone product will depend upon (i) the mode of ring cleavage by the thiol reagent and (ii) the mode of addition of the sulfenyl chloride to the double bond in the alkenyl succinic acid, ester or amide reactant.

With sulfur halides ($S_xCl_2$, where x is 1–4), thio, dithio and polythio bis-lactones are formed. Subsequent reaction of the latter with THAM affords the corresponding thio-bis-lactone oxazoline products.

Oxidation of the mono-thio-bis-lactones with peroxides can yield both sulfoxides and sulfones. In the case of the dithio-bis-lactones, oxidation affords sulfo-containing lactones.

In another approach thiyl lactones can also be designed by addition of the sulfenyl chloride reagent to the alkenyl succinic anhydride. Lactonization of the adduct can then be effected by either reacting (i) the sulfenyl chloride adduct per se, or (ii) the dehydrohalogenated adduct with an alcohol, water or an amine. Lactonization of the dehydrohalogenated thiyl substituted anhydride via option (ii) is preferably conducted in the presence of an acid catalyst.

Examples of useful thiols in preparing thiyl lactones via epoxide cleavage include alkyl and aryl thiols and heterocyclic thiols such as 2-mercapto-benzothiazole. Dithiophosphoric acids e.g. $(RO)_2P(=S)$—SH, are also useful in designing phosphorus-containing products. In an alternate synthetic approach, the sulfenyl chloride analogs of the above-described thiols can be added to alkenyl succinic acid analogs to give the desired thiyl-substituted lactone reagents.

In another embodiment of the present invention, the reaction of chlorosulfonic acid or its equivalent, e.g. $SO_3$ and its complexes, with alkenylsuccinic anhydrides gives adducts which upon hydration yield sulfo lactone acids. Treatment of the latter with THAM can under suitable conditions generate sulfo lactone oxazoline end-products.

In still another embodiment, lactam carboxylic acids are used in the design of lactam oxazoline additives.

THE AMINO ALCOHOL

The amino alcohol used to react with the lactone to provide the oxazoline ring is a 2,2-disubstituted-2-amino-1-alkanol containing a total of 4 to 8 carbon atoms, and which can be represented by the formula:

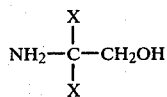

wherein X is hydrogen, an alkyl, or hydroxy alkyl group, with at least one of the X substituents, and preferably both of the X substituents, being a hydroxy alkyl group, with at least one of the X substituents, and preferably both of the X substituents being a hydroxy alkyl group of the structure $-(CH_2)_nOH$, wherein n is 1 to 3.

Examples of such 2,2-disubstituted amino alkanols, include 2-amino-2-methyl-1,3-propanediol, 2-amino-2-(hydroxymethyl)-1,3-propanediol (also known as tris-hydroxyaminomethane or THAM), 2-amino-2-ethyl-1,3-propanediol, etc. Because of its effectiveness availability, and cost, the THAM is particularly preferred.

By sharp contrast, we have found that other amino alcohols such as ethanolamine, propanolamine and butanolamine which lack 2,2-disubstitution, do not afford oxazoline products. Similarly, the prior art (British Pat. No. 1,420,962) clearly teaches that ethanolamine reacts with lactone acids to give amide derivatives via cleavage of the lactone ring. We have discovered that interaction of lactone acids, esters and amides with 2,2-disubstituted amino alcohols is unique, in that the lactone ring of the reactant remains intact and novel lactone oxazoline products are formed exclusively.

THE OXAZOLINE REACTION CONDITIONS

The formation of the novel oxazoline materials in a very high yield, can be effected by adding at least about 1 molar equivalent of the aforesaid 2,2-disubstituted-2-amino-1-alkanol per mole equivalent of the polyalkyl lactone acid, ester or amide with or without an inert diluent, and heating the mixture at 100°-240° C., preferably 170°-220° C. until reaction is complete by infra-red analysis of the product showing maximal absorption for oxazoline.

Although not necessary, the presence of small amounts such as 0.01 to 2 wt. %, preferably 0.1 to 1 wt. %, based on the weight of the reactants, of a metal salt can be used in the reaction mixture as a catalyst. The metal catalyst can later be removed by filtration or by washing a hydrocarbon solution of the product with a lower alcohol, such as methanol, ethanol, isopropanol, etc., or an alcohol/water solution.

Alternatively, the metal salt can be left in the reaction mixture, as it appears to become stably dispersed, or dissolved, in the reaction product, and depending on the metal, it may even contribute performance benefits to the oil or gasoline. This is believed to occur with the use of zinc catalysts in lubricants.

Inert solvents which may be used in the above reaction include hydrocarbon oils, e.g. mineral lubricating oil, kerosene, neutral mineral oils, xylene, halogenated hydrocarbons, e.g., carbon tetrachloride, diochlorobenzene, tetrahydrofuran, etc.

Metal salts that may be used as catalysts in the invention include carboxylic acid salts of Zn, Co, Mn and Fe. Metal catalysts derived from strong acids (HCl, sulfonic acid, $H_2SO_4$, $HNO_3$, etc.) and bases, tend to diminish the yield of the oxazoline products and instead favor imide or ester formation. For this reason, these strong acid catalysts or basic catalysts are not preferred and usually will be avoided. The carboxylic acids used to prepare the desired catalysts, include $C_1$ to $C_{18}$, e.g., $C_1$ to $C_8$ acids, such as the saturated or unsaturated mono- and dicarboxylic aliphatic hydrocarbon acids, particularly fatty acids. Specific examples of such desired carboxylic acid salts include zinc acetate, zinc formate, zinc propionate, zinc stearate, manganese(ous) acetate, iron tartrate, cobalt(ous) acetate, etc. Completion of the oxazoline reaction can be readily ascertained by using periodic infrared spectral analysis for following oxazoline formation ($C{=}N$ absorption band at 6.0 microns) until maximized relative to lactone absorption or by the cessation of water evolution.

REACTION MECHANISM OF THE OXAZOLINE FORMATION

While not known with complete certainty, but based on experimental evidence, it is believed that the reaction of the alkyl lactone material, e.g., a substituted lactone acid, ester or amide with the amino alcohol of the invention, e.g. 1 to 1.5 molar equivalents of 2,2-disubstituted-2-aminoethanol such as tris-hydroxymethylamino methane (THAM), gives lactone oxazoline ring structures as portrayed above.

USE OF THE POLYALKYL LACTONE-OXAZOLINE ADDITIVE IN OLEAGINOUS COMPOSITIONS

The oil-soluble lactone oxazoline reaction products of the invention can be incorporated in a wide variety of oleaginous compositions. They can be used in lubricating oil compositions, such as automotive crankcase lubricating oils, automatic transmission fluids, etc. in concentrations generally within the range of about 0.01 to 20 weight percent, e.g. 0.1 to 10 weight percent, preferably 0.3 to 3.0 weight percent, of the total composition. The lubricants to which the lactone-oxazoline products can be added include not only hydrocarbon oils derived from petroleum but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used as multifunctional additives having detergency, anti-rust properties in petroleum fuels such as gasolines, kerosene, diesel fuels, No. 2 fuel oil and other middle distillates, a concentration of the additive in the fuel in the range of 0.001 to 0.5 weight percent, based on the weight of the total composition, will usually be employed.

When used as an antifoulant in oil streams in refinery operations to prevent fouling of process equipment such as heat exchangers or in turbine oils, about 0.001 to 2 wt. % will generally be used.

The additive may be conveniently dispensed as a concentrate comprising a proportion of the additive, e.g., 20 to 90 parts by weight, dissolved in a proportion of a mineral lubricating oil, e.g., 10 to 80 parts by weight, with or without other additives being present.

In the above compositions or concentrates, other conventional additives may also be present including dyes, pour point depressants, antiwear agents such as tricresyl phosphate or zinc dialkyldithiophosphates of 3 to 8 carbon atoms in each alkyl group, antioxidants, such as N-phenyl α-naphthylamine, tert-octylphenol sulfide, 4,4'-methylene bis(2,6-di-tert-butyl phenol), viscosity index improvers such as ethylene-propylene co-polymers, polymethacrylates, polyisobutylene, alkyl fumarate-vinyl acetate copolymers and the like, deemulsifiers such as polysiloxanes, ethoxylated polymers and the like.

This invention will be further understood by reference to the following examples, which include preferred embodiments of the invention.

SIMPLE LACTONE REACTANTS

EXAMPLE 1 (DIBASALAC)

Thirty grams (0.143 mole) of diisobutenyl succinic anhydride (DIBSA) which can be a mixture of three isomers (A, B, and C), depending on the mode of synthesis, were combined

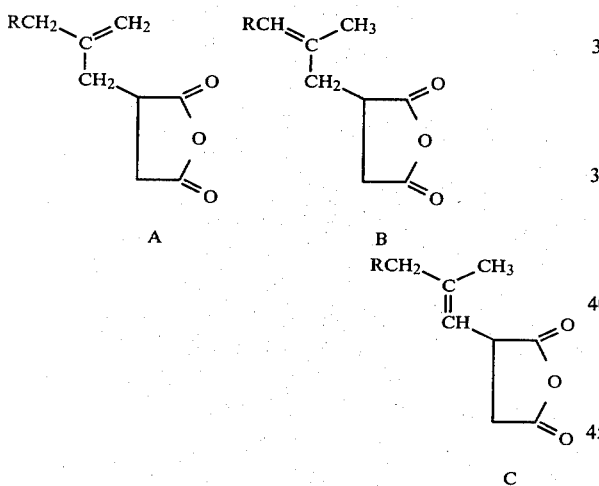

R = t-Bu with 2.6 g of water and three drops of concentrated sulfuric acid. The mixture was heated to 110°–120° C. for one hour. Infrared analysis of the reaction mixture showed that lactone formation was virtually complete. The addition of 200 ml of ether and subsequent cooling of the resulting ether solution caused solids to separate from solution. Three crops of white solid amounting to 27.1 g were collected and recrystallized from ether-acetone solution. The product, m.p. 141°–142° C., featured an IR spectrum with intense carbonyl absorption bands at 5.70 (lactone) and 5.82 (carboxylic acid) microns and analyzed for 62.78% C and 9.14% H (Theory: 63.13% C and 8.86% H). The product, dibsalac, presumably could be one or more of the isomeric lactones depicted below. The proton and IR spectral data suggest that the 5-ring lactone acid products

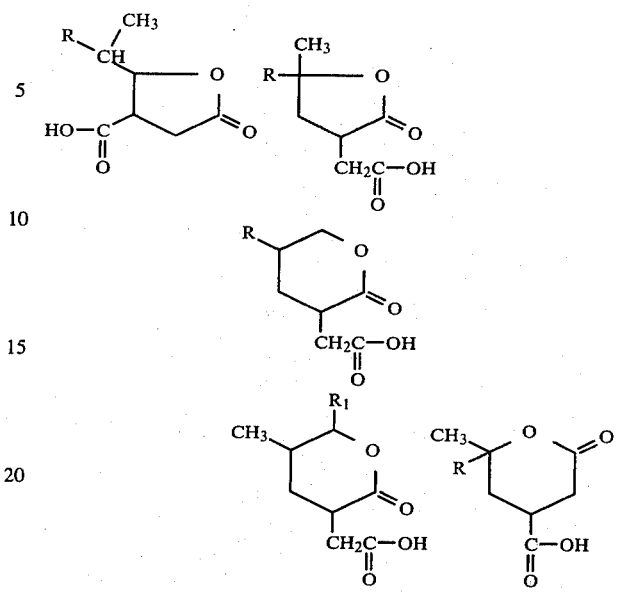

predominate when reactant A is employed in the lactonization process.

EXAMPLE 2 (NOSALAC)

One mole (210 g) of n-2-octenylsuccinic anhydride (nosa) and 1.1 mole (20 g) of water were combined and heated at 100°–110° C. for about a half hour. A quantitative conversion to n-2-octenylsuccinic acid occurred. Five drops of concentrated sulfuric acid were added to the latter, and the mixture was then heated for 16 hours at about 155° C. Upon cooling, the liquid product gradually crystallized. The white solids, m.p. 94°–95° C., were isolated in high yield and featured an IR spectrum with strong absorption bands at 5.65 and 5.82 microns. The lactone acid analyzed for 63.49% C and 8.35% H, and judging from its IR spectrum (carbonyl absorption at 5.65 microns) is mainly a 5-ring lactone although some 6-ring lactone products can also form depending upon reaction conditions. Plausible lactone structures (for nosalac) are featured below:

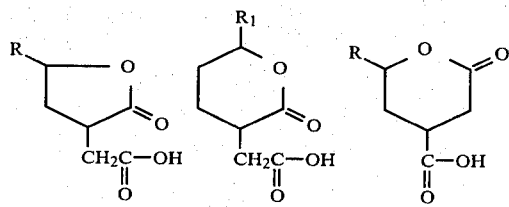

R = n-hexyl; $R_1$ = n-pentyl

EXAMPLE 3 (TPSALAC)

A mixture of 405 g (1.52 moles) of tetrapropenylsuccinic anhydride (TPSA) and 30 g (1.66 moles) of water were heated to 100°–110° C. for a half hour. Infrared analysis of the reaction mixture indicated complete conversion of the anhydride to tetrapropenylsuccinic acid.

The mixture was treated with 40 g of Amberlyst 15 catalyst and heated to 125°–130° C. overnight. Infrared analysis indicated that lactonization was complete. The lactone acid product (tpsalac) was dissolved in ether and filtered to remove the catalyst. Rotoevaporation of the supernatant gave an oily concentrate which featured an IR spectrum with intense lactone and carboxylic acid carbonyl absorption bands.

EXAMPLE 4 (OSALAC)

A half mole (175 g) of 2-octadecenyl succinic anhydride (osa) and 0.55 mole (10 g) of water were mixed and heated in a reaction flask for a half hour at 80° C. Infrared analysis showed that complete conversion of the anhydride to succinic acid had occurred. While stirring at 80° C., 0.5 g of concentration sulfuric acid was added, and the reaction temperature was increased to 130°–140° C. Heating at 140° C. for 1.5 hours completely converted the dicarboxylic acid to the desired lactone acid products. When the cooled mixture was diluted with ether a white solid separated from solution. Infrared analysis of the isolated solids revealed the presence of a 5-ring lactone acid (strong bands at 5.67 and 5.82 microns). Cooling the supernatant gave more solids. Further fractional crystallization of later crops afforded 6-ring lactone acid products. The combined weight of all crops revealed that the yield of lactone acid product (osalac) was quantitative. A recrystallized sample of 5-ring lactone product melted at 112° C. and analyzed for 71.50% carbon, 10.77% H and 16.67% oxygen. Theory requires 71.49% C, 11.18% H, and 17.32% O.

EXAMPLE 5 (PIBSALAC)

One hundred twenty grams of polyisobutenyl succinic anhydride (pibsa) of MW$\approx$960 and having a saponification number (Sap. No.) of 92 were diluted in 100 ml of tetrahydrofuran (THF). Two grams of water were added and the resulting mixture was heated to reflux temperature for about two hours. Infrared analyses of the mixture showed that the anhydride was fully converted to the succinic acid analog. The THF solvent was boiled off and 1 ml of concentrated sulfuric acid was added to the mixture at about 110° C. Heating for two hours at 120° C. effected the conversion of the polyisobutenyl succinic acid to the desired lactone acid product (pibsalac). Infrared analyses showed the presence of strong absorption bands at about 6.5–8.5 microns.

The mixture was diluted in 200 ml of hexane, washed twice with 200 ml of water and subsequently concentrated by rotoevaporation for two hours at 80° C. Infrared analysis of the lactone acid product treated with diethylamine featured an intense absorption band at 5.64 microns (5-ring lactone carbonyl stretching).

EXAMPLE 6 (PIBSALAC)

A mixture of one hundred grams of polyisobutenyl succinic acid as prepared in Example 5 and 10 g of Amberlyst 15 catalyst were heated at about 100° C. for about eight hours, and then at 120° C. for a half hour. Infrared analysis showed the presence of lactone acid. The product was diluted with hexane, filtered, and rotoevaporated at 80° C. for four hours. The residue upon treatment with an excess of diethylamine featured an infrared spectrum with a strong lactone carbonyl absorption band at 5.64 microns.

EXAMPLE 7 (PIBSALAC)

A mixture of 140 g (0.1 mole) of polyisobutenyl succinic anhydride (MW$\approx$960 and having a saponification number [Sap. No.] of 92), 3 g of water and 1 g of concentrated sulfuric acid were heated for about three hours at 105° C. Infrared analysis indicated that the anhydride was directly and completely converted to the desired lactone acid as evidenced by the strong carbonyl absorption bands at 5.63 to 5.84 microns. The reaction product was treated with 0.02 mole of NaOH (dissolved in tetrahydrofuran) filtered and rotoevaporated at 80° C. for four hours. The IR spectrum of the amber concentrate treated with an excess of diethylamine showed a strong lactone carbonyl absorption at 5.65 microns.

EXAMPLE 8 (NOSALAC ESTER)

A half-mole (105 g) of n-octenylsuccinic anhydride and 23 g of absolute ethanol were combined and gradually heated to 100° C. over a half-hour period. A milliliter of concentrated sulfuric acid was added and heating at 120° C. was continued for 30 hours. Infrared analysis indicated virtually complete conversion to lactone ester. Upon standing, the product partially solidified. Recrystallization of the crude solid from hexane afforded a crystalline material, m.p. 83° C., which featured an infrared spectrum with intense lactone and ester carbonyl absorption bands at 5.63 and 5.80 microns.

EXAMPLE 9 (DIBSALAC AMIDE)

The dropwise addition of a tenth mole (7.3 g) of diethylamine to 0.1 mole (21 g) of diisobutenylsuccinic anhydride in 100 ml of ether gave the amic acid directly. Three drops of concentrated sulfuric acid was added to the reaction mixture which was freed of ether solvent and heated to about 200° C. for 10 hours. Infrared analysis revealed the presence of lactone amide. The product was diluted in ether and washed with aqueous $Na_2CO_3$. The ether solution was dried over solid $Na_2CO_3$ and rotoevaporated.

Distillation of a portion of the concentrated product gave a fraction, b.p. 170° C. (0.1 mm), which featured an infrared spectrum with very strong absorption bands at 5.62 (lactone) and 6.08 (amide) microns, and analyzed for 4.90% nitrogen. Theory required 4.94% nitrogen.

EXAMPLE 10 (NOSALAC AMIDE)

Twenty-eight grams of the lactone acid product prepared in Example 2 (mainly n-hexyl butyrolactone-α-acetic acid) were treated with an excess of gaseous ammonia at 180° C. for about two hours. The product was dissolved in hot xylene and filtered. Upon cooling the solution, a solid product precipitated. The dried product (15 g) melted at 117°–119° C., showed an IR spectrum with dominant bands at 5.65 and 6.0 microns and analyzed for 62.75% C, 9.29% H and 6.18% N. Theory for the lactone amide requires 63.40% C, 9.31% H and 6.18% N.

EPOXY ANHYDRIDE REACTANTS

EXAMPLE 11 (EPOXY-DIBSA)

Gram portions of 0.05 mole of meta-chloroperbenzoic acid (70% purity) were added over a half-hour period to 0.05 mole (10.1 g) of diisobutenylsuccinic anhydride dissolved in 300 ml of methylene chloride maintained at 0° C. As the mixture warmed to room temperature, it became clear and then clouded as m-chlorobenzoic acid byproduct separated from the solution. The mixture was stirred overnight at room temperature. The mixture was filtered, and the supernatant was washed with a 5% aqueous Na2CO3 solution twice, dried over Na2SO4, and concentrated by rotoevaporation. During evaporation, a solid separated from solution. The white solid (9.4 g) melted at 94°–97° C. and analyzed for 7.9% oxygen (theory required 8.01% oxygen). The spectral data were consistent with

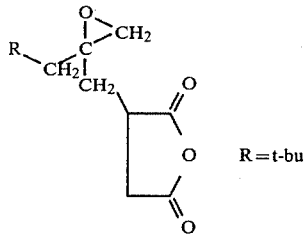

EXAMPLE 12 (EPOXY PIBSA)

Approximately 0.2 mole (240 g) of polyisobutenyl-succinic anhydride (MW ≈ 960) having a saponification number of approximately 84 was dissolved in one liter of $CH_2Cl_2$ at 25° C., the well-stirred solution was treated with 5 g portions of 0.2 mole (40.6 g) of m-chloroperbenzoic acid over an hour period. An exothermic reaction ensued, and raised the temperature of the reaction mixture to 34° C. Upon standing overnight, m-chlorobenzoic acid separated from solution. Filtration gave a clear $CH_2Cl_2$ solution which was washed with aqueous 5% $Na_2CO_3$ solution, and distilled water, and then dried over $CaCl_2$. Rotoevaporation at 70° C. for two hours afforded 242 g of epoxy PIBSA as an amber oil.

EXAMPLE 13 (EPOXY PIBSA)

Two hundred grams of polyisobutenylsuccinic anhydride of MW ≈ 1300 having a sponification number of about 100 were dissolved in a liter of $CH_2Cl_2$ and 40.5 g (0.2 mole) of m-chloroperbenzoic acid (85%) were added portionwise over an hour period to the well-stirred reaction mixture at room temperature. The exothermic reaction caused the temperature of the mixture to peak to 33° C. The clear solution was allowed to stir at ambient temperature for five hours. During this period, white solids separated from solution. The solids were removed by filtration, and the supernatant was freed of $CH_2Cl_2$, and diluted in hexane and filtered. Rotoevaporation at 80° C. for two hours gave a concentrate (180 g) which was diluted in 90 g of neutral oil.

HYDROXYL-CONTAINING LACTONE REACTANTS

EXAMPLE 14 (HYDROXY DIBSALAC)

A mixture of ca. 0.01 mole (2.76 g) of epoxy dibsa as described in Example 11 and 0.2 g of $H_2O$ was dissolved in 5 ml of tetrahydrofuran (THF) and heated to reflux for an hour. IR analysis indicates complete conversion of the epoxy anhydride to 5- and 6-ring hydroxy lactone carboxylic acids:

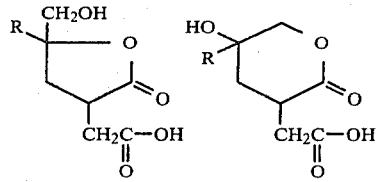

R = neo-pentyl

The synthesis of the latter was also achieved by simply combining equimolar amounts (0.1 mole) of dibsa, hydrogen peroxide (30%) and a catalytic amount of sulfuric acid (1 drop) in 100 ml tetrahydrofuran (THF) and refluxing the mixture for several hours.

Addition of ether to the reaction mixture induced the separation of solid product. Filtration gave a solid which featured an infrared spectrum with intense lactone and carbonyl absorption bands. Recrystallization from ether gave a solid which melted at 180° C. and analyzed for 59.29% carbon, 8.28% hydrogen and 32.57% oxygen. Theory for the hydroxy lactone carboxylic acid requires 59.00% C, 8.25% H and 32.75% O.

EXAMPLE 15 (HYDROXY PIBSALAC)

A mixture comprising 0.32 mole (410 g) of pibsa (MW ≈ 960) with a saponification number of 83, 0.32 mole (36.3 g) hydrogen peroxide (30% aqueous solution) and 0.4 g (0.1 wt.% of concentrated sulfuric acid was heated with stirring at about 120° C. for approximately five hours. Infrared analysis showed the presence of carbonyl bands ascribable to lactone acid. The product was diluted with an equal volume of neutral oil.

EXAMPLE 16 (HYDROXY DIBSALAC ESTER)

A tenth mole (22.6 g) of monomethyl diisobutenyl succinate and 0.1 mole (11.4 g) of 30% hydrogen peroxide were combined with 4.6 g of formic acid and heated to about 50° C. with stirring. Infrared analysis of the reaction mixture after two hours reaction at 50° revealed that the hemi-ester was completely converted to the desired hydroxyl containing lactone ester. The same ester was also obtained by (i) epoxidation of monomethyl diisobutenyl succinate with m-chloroperbenzoic acid or (ii) methanolysis of epoxy dibsa prepared in Example 11. The proposed structure for the major hydroxyl-containing lactone ester generated via the three synthetic schemes is methyl γ-neo-pentyl-γ-hydroxymethylbutyrolactone-α-acetate:

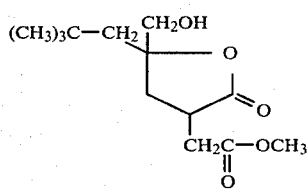

Treatment of the latter with an equimolar portion of morpholine gave a product which featured an IR spectrum identical to that for the hydroxy lactone amide obtained in Example 19.

EXAMPLE 17 (HYDROXY PIBSALAC ESTER)

A tenth mole (121 g) of epoxy pibsa prepared in Example 12 and 0.1 mole (13.4 g) of n-octanol were heated together for about 12 hours. The product was diluted with an equal weight of neutral oil and filtered. The infrared spectrum of the oil-diluted product featured the expected lactone and ester carbonyl absorptions at 5.62 and 5.74 microns.

EXAMPLE 18 (HYDROXY DIBSALAC AMIDE)

An ether solution of 0.01 mole (0.87 g) of morpholine was added dropwise to an ether solution of 0.01 mole (2.26 g) of epoxy dibsa (Example 11) at about 25° C. The addition was exothermic and caused the ether to reflux during addition. Upon cooling, solids formed. Infrared analysis of the isolated solid (0.4 g) showed sharp bands at 3.03 (hydroxyl), 5.80 (lactone) and 6.08 (amide) microns indicative of the hydroxyl-containing 6-ring lactone amide. The residue from the supernatant (ca. 2.4 g) featured an IR spectrum consistent with the 5-ring lactone product. The solid product m.p. 94–97 analyzed for 62.07% C, 8.60% H, and 4.74% N. Theory for the hydroxy lactone amide requires 61.32% C, 8.69% H, and 4.47% N.

EXAMPLE 19 (HYDROXY PIBSALAC AMIDE)

A tenth mole (121 g) of epoxy pibsa prepared in Example 12 was dissolved in 100 ml of $CH_2Cl_2$, and 0.1 mole (9.0 g) of morpholine was added to it dropwise. The addition was exothermic. The mixture was then heated at 80° C. for 12 hours, and at 130° C. for an additional 6 hours. The product analyzed for 0.83% N, and feature an IR spectrum with prominent bands at 5.61 and 6.02 microns as expected for a lactone amide.

THIYL-SUBSTITUTED LACTONE REACTANTS

EXAMPLE 20 (ADDUCT OF $SCl_2$ AND n-OCTENYLSUCCINIC ANHYDRIDE)

Three moles (630 g) of n-octenylsuccinic anhydride were diluted in a liter of $CH_2Cl_2$ and stirred at room temperature. Then 1.5 moles (154 g) of $SCl_2$ in 500 ml of $CH_2Cl_2$ were added dropwise. The exothermic reaction peaked to 50° C. initially and external cooling was applied to maintain reaction temperature at about 25° C. No HCl evolution occurred. After stirring the reaction mixture for an hour after the $SCl_2$ addition, the solvent was removed by evaporation with a mild stream of nitrogen. The solid that separated from solution during solvent evaporation was isolated (40 g) and after being recrystallized from $CH_2Cl_2$, melted at 149°–150° C. and analyzed for 55.45% C, 7.17% H, 5.73% S and 11.4% Cl. The adduct, $C_{24}H_{26}O_6SCl_2$ requires 55.06% C, 6.93% H, 6.13% S, and 13.55% Cl. The infrared spectrum featured an intense anhydride absorption at 5.67 microns, and a proton spectrum was consistent with the structure shown below.

The concentrate obtained from the supernatant weighed 745 g and featured an IR spectrum similar to that shown for the solid. The yield of adduct was virtually quantitative. One possible structure shown below.

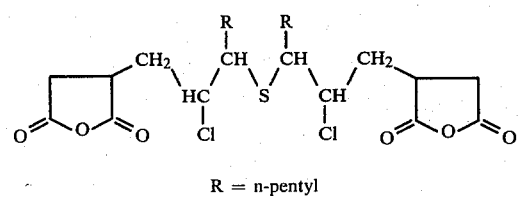

R = n-pentyl

EXAMPLE 21 ($S_2Cl_2$-n-OCTENYLSUCCINIC ANHYDRIDE ADDUCT)

A mole (210 g) of n-octenylsuccinic anhydride was dissolved in a liter of ether and a half mole (67.5 g) of sulfur monochloride ($S_2Cl_2$) was added dropwise to the stirred solution at room temperature. An exothermic reaction occurred and the addition was completed under refluxing conditions. The reaction mixture was stirred overnight and then concentrated by rotoevaporation at 50° C. for 2 hours. The product featured an IR spectrum with a prominent anhydride carbonyl band at 5.65 microns, and analyzed for 49.33% C, 6.04% H, 10.7% S and 12.6% Cl. Theory for the $S_2Cl_2$-n-octenylsuccinic anhydride adduct ($C_{24}H_{36}Cl_2O_6S_2$) requires 51.88% C, 6.53% H, 11.54% S, and 12.76% Cl.

EXAMPLE 22

Two-tenths (30.4 g) mole of cis-1,2,3,6-tetrahydrophthalic anhydride (cis-4-cyclohexene-1,2-dicarboxylic anhydride) was dissolved in chloroform (200 ml) and 0.1 mole (10.3 g) of $SCl_2$ were added dropwise to the well stirred solution at room temperature. The $SCl_2$ addition increased the temperature to 53° C. and the addition was completed at about 53° C. Midway during $SCl_2$ addition the solution turned hazy and some solids separated from solution. After addition the mixture was allowed to cool and the solids (20 g) were isolated by filtration. The solid product featured an IR spectrum with strong anhydride carbonyl absorption, melted at 177°–178° C., and analyzed for 46.88% C, 4.22% H, 7.68% S, and 14.93% Cl. Theory for the adduct ($C_{16}H_{16}Cl_2O_6S$) requires 47.18% C, 3.96% H, 7.87% S, and 17.41% Cl.

EXAMPLE 23 (THIO-BIS-OSALAC)

Two-tenths mole (73.6 g) of octadecenyl succinic acid was dissolved in 500 ml ether and a tenth mole (10.3 g) of $SCl_2$ was added dropwise to the stirred ether solution at about 25° C. The addition was exothermic (ether refluxed) and HCl evolution occurred. The mixture was refluxed for about 8 hours. Upon cooling solids separated from solution. The solid product featured an infrared spectrum with prominent lactone and carboxylic acid carbonyl absorptions at 5.62 and 5.82 microns, melted at 158°–163°, and analyzed for 69.01% C, 10.17% H, 4.37% S and 16.74% O. Theory for the lactone acid ($C_{44}H_{78}O_8S$) requires 68.88% C, 10.25% H, 4.18% S and 16.69% O.

Further refluxing the supernatant gave four more crops of product with a combined weight of 50 g. The yields were quantitative. The proposed structure for thio-bis-osalac is illustrated below.

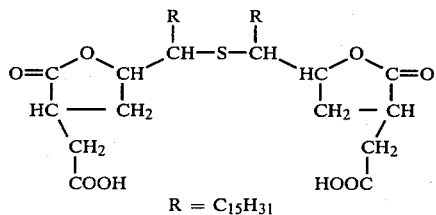

R = C₁₅H₃₁

EXAMPLE 24 (DITHIO-BIS-OSALAC)

Two hundred grams (0.54 mole) of n-octadecenyl succinic acid were dissolved in a liter of $CHCl_3$ and 36.7 g (0.272 mole) of sulfur monochloride ($S_2Cl_2$) were added dropwise to the stirred solution at room temperature. The exothermic process was accompanied by vigorous HCl evolution. After refluxing the mixture for about eight hours, the solution was cooled and solids separated. Filtration gave 19 g of solid (m.p. 131°–136° C.) which featured an IR spectrum with intense carbonyl bands at 5.62 and 5.72 microns, and analyzed for 66.42% C, 9.63% H, and 8.22% S. Theory for the adduct ($C_{44}H_{78}O_8S_2$) requires 66.12% C, 9.84% H, and 8.02% S. Rotoevaporation of the supernatant gave a solid product in high yield. The proposed structure for dithio-bis-osalac is given below.

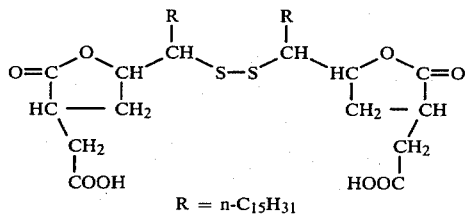

R = n-C₁₅H₃₁

EXAMPLE 25 (THIO-BIS-DIBSALAC)

Two tenths mole (42.0 g) of dibsa was dissolved in 100 ml. of THF and 0.1 mole (10.3 g) of $SCl_2$ were added. During addition the reaction temperature climbed to about 35° C. and HCl evolution occurred. The mixture was refluxed for four hours and then heated to 100° (THF distilled off) for two more hours to effect complete dehydrohalogenation.

The residue was cooled and dissolved in THF and 0.2 mole of water and two drops of concentrated sulfuric acid were added. The mixture was refluxed for several hours. Infrared analysis revealed complete conversion to the desired thio-bis-lactone acid.

EXAMPLE 26 (THIO-BIS-PIBSALAC)

Approximately 130 g of polyisobutenylsuccinic acid (MW ≈ 960 (prepared via hydrolysis of PIBSA having a saponification number of ca 84) were dissolved in 400 ml of chloroform and 0.05 mole (5.3 g) of $SCl_2$ was added dropwise to the stirred solution. After refluxing the mixture overnight, two drops of sulfuric acid were added, the solvent was stripped off, and the mixture heated at about 100° C. overnight. The product featured an infrared spectrum with strong absorption bands in the 5.6–5.8 micron region and analyzed for 1.69% sulfur and 0.09% chlorine. The IR spectrum of the diethylamine-treated product revealed a strong lactone carbonyl band at 5.63 microns.

EXAMPLE 27 (THIO-BIS-PIBSALAC)

A tenth mole (130 g) of polyisobutenylsuccinic anhydride (MW ≈ 960) having a saponification number of approximately 84 was dissolved in 100 ml of dioxane and 0.05 mole (5.3 g) of $SCl_2$ were added dropwise to the well-stirred solution at ca 25° C. The mixture was then refluxed for four hours (HCl evolution noted). At this point, 4 g of water acidified with three drops of concentrated sulfuric acid were added and the mixture was further refluxed for 24 hours. The mixture was filtered through basic celite and rotoevaporated at 90° C. for several hours. The concentrate featured an IR spectrum with strong absorption bands in the 5.6–5.8 micron region, and analyzed for 1.55% sulfur and 0.09% chlorine.

EXAMPLE 28 (THIO-BIS-NOSALAC ESTER)

A half mole of the adduct of $SCl_2$ and n-octenylsuccinic anhydride described in Example 20 was added to 500 ml of xylene containing 32 g of methanol. The mixture was allowed to stir overnight and heated to reflux for about four hours. The product was then rotoevaporated for three hours at 70°–80° C. The final product featured an IR spectrum with intense lactone and ester carbonyl absorption at 5.63 and 5.78 microns, and analyzed for 60.48% carbon, 8.30% hydrogen, and 6.48% sulfur. The thio-bis-lactone ester $(C_{26}H_{42})_8S$ requires 60.67% C, 8.23% H and 6.23% S.

The same ester lactone was easily prepared via the addition of $SCl_2$ to the mono-methyl ester of n-octenyl succinic acid.

EXAMPLE 29 (DITHIO-BIS-NOSALAC ESTER)

Four-tenths mole of the adduct of $S_2Cl_2$ and n-octenylsuccinic anhydride described in Example 21 and 0.8 mole (25.6 g) of methanol were dissolved in 200 ml of chloroform and stirred at room temperature for four days, refluxed for 16 hours, and roto-evaporated at 80° C. for three hours. The product showed an IR spectrum with intense lactone and ester carbonyl bands and analyzed for 57.19% carbon, 7.93% hydrogen, and 10.54% sulfur. Theory for the dithio-nosalac methyl ester $(C_{26}H_{42}O_8S_2)$ requires 57.11% carbon, 7.74% hydrogen and 11.73% sulfur.

EXAMPLE 30 (THIO-BIS-DIBSALAC ESTER)

A tenth mole of mono-methyl diisobutenylsuccinate was dissolved in 100 ml of xylene and 0.05 mole of $SCl_2$ was added dropwise to the stirred xylene solution. The mixture was refluxed overnight and rotoevaporated for three hours at 90° C. IR analysis revealed that the hemi-ester/$SCl_2$ adduct was completely converted to the desired thio-bis-lactone methyl ester. A plausible structure for the sulfurbridged bis-lactone is shown below:

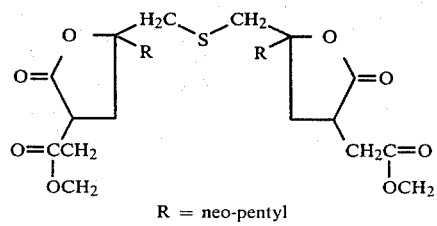

R = neo-pentyl

EXAMPLE 31 (THIO-BIS-NOSALAC AMIDE)

A tenth mole (51.3 g) of the adduct of SCl$_2$ and n-octenyl succinic anhydride described in Example 20 was dissolved in 100 ml chloroform, and 0.2 mole (14.6 g) of diethylamine was added dropwise to the well-stirred solution at room temperature. The exothermic reaction caused the reaction temperature to peak to about 50° C., and external cooling was applied to maintain reaction temperature at about 10° C. The cooling bath was removed, and the reaction mixture was refluxed for two hours. The evolution of HCl gas occurred. The mixture was rotoevaporated for an hour at 80° C. and diluted with 200 ml of ether. Filtration removed the Et$_2$NH.HCl salt that formed. The filtrate was washed with aqueous Na$_2$CO$_3$ (5% soln.) and dried over Na$_2$CO$_3$. Rotoevaporation of the ether solution gave a residue which featured an IR spectrum with prominent lactone and amide carbonyl absorption bands at 5.62 and 6.10 microns, and analyzed for 63.73% C, 9.36% H, 4.69% N and 5.37% S. Theory for the thio-bis-lactone amide (C$_{32}$H$_{56}$N$_2$O$_6$S) requires 64.39% C, 9.45% H, 4.69% N and 5.37% S.

EXAMPLE 32

A tenth mole of mono-methyl diisobutenyl succinate was dissolved in 100 ml of xylene and a tenth mole (23.5 g) of 2,4-dinitrobenzenesulfenyl chloride (dissolved in 100 ml xylene) was added dropwise. The reaction mixture was then refluxed overnight (HCl evolution occurred). The mixture was rotoevaporated using high vacuum at 90° C. for four hours. The residue, featured an IR spectrum with strong lactone and ester carbonyl absorption bands at 5.63 and 5.73 microns.

EXAMPLE 33 (DIBMALAC ESTER)

0.05 mole (10.4 g) of diisobutenyl maleic anhydride (from diisobutylene and 2-chloro maleic anhydride) and 0.05 mole (2.4 g) of absolute ethanol were combined and heated to 95° C. to generate the hemi-ester. At this point, a drop of sulfuric acid (95%) was added and the stirred mixture heated at 100° C. for about an hour. The product (in ether) was washed with aqueous Na$_2$CO$_3$ (5% solution) and dried over Na$_2$CO$_3$. Vacuum distillation of the crude product afforded 7.0 g of distillate, b.p. 118°–119° C. (0.15 mm) which featured an IR spectrum with intense lactone and ester carbonyl absorption bands at 5.63 and 5.7 microns. The distilled product analyzed for 66.07% carbon and 8.73% hydrogen. Theory for the dibma lactone ester (C$_{14}$H$_{22}$O$_4$) requires 66.11% carbon and 8.72% hydrogen.

LACTONE OXAZOLINES

EXAMPLE 34—(DIBSALAC OXAZOLINE)

Eleven grams (0.045 mole) of DIBSALAC described in Example 1 were dissolved in 20 ml of xylene and 4.65 g (0.048 mole) of 2-amino-2-methyl-1-propanol was added dropwise. The reaction mixture was heated to reflux in a flask equipped with a Dean-Stark moisture trap. After 16 hours, 1.5 ml of water were collected and the xylene was removed by rotoevaporation. Vacuum distillation of the residue afforded a colorless liquid, b.p. 135° C. (0.3 mm) in about 85% yield. The liquid gradually crystallized on standing. The crystalline product featured an infrared spectrum with prominent lactone and oxazoline absorption bands at about 5.68 and 6.02 microns, and analyzed for 68.15% carbon, 9.48% hydrogen, 4.93% nitrogen and 16.54% oxygen. Theory for the lactone oxazoline (C$_{16}$H$_{27}$NO$_3$) requires 68.28% carbon, 9.6% hydrogen, 4.99% nitrogen and 17.06% oxygen. The proposed structure is shown below.

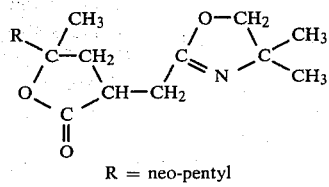

R = neo-pentyl

EXAMPLE 35—(DIBSALAC OXAZOLINE)

DIBSALAC (0.05 mole, 11.4 g) described in Example 1 and 0.05 mole (6.2 g) of tris-(hydroxymethyl)-aminomethane (THAM) were added to 25 ml of xylene in a reactor equipped with a Dean-Stark moisture trap. The mixture was refluxed until ca. 1.6 ml of water were collected in the moisture trap (approximately 5 hours). Infrared analysis indicated complete conversion to lactone oxazoline product. Upon cooling to room temperature, the clear solution became cloudy and white solids separated from solution. The solid product was filtered off, washed several times with ether, and dried. The first crop weighed 6.0 grams and melted at 82°–88° C. Recrystallization from xylene gave a white solid which melted at 97°–103° C., and featured an IR spectrum with prominent lactone carbonyl and oxazoline (C=N) absorption bands at 5.66 and 6.0 microns. The recrystallized solid analyzed for 59.87% C, 8.46% H, and 4.26% N. Theory for the lactone oxazoline hemi-hydrate (C$_{16}$H$_{24}$NO$_5$.½H$_2$O) requires 60.15% C, 7.89% N, and 4.38% N. The product can be represented by the following structure:

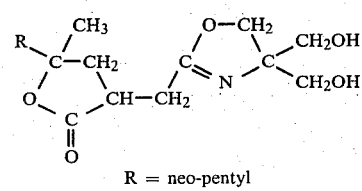

R = neo-pentyl

EXAMPLE 36—(NOSALAC OXAZOLINE)

Nosalac amide (0.025 mole, 5.67 g) described in Example 10 and 0.025 mole (3.0 g) of THAM were added to 10 ml of xylene and the mixture was refluxed overnight. The solvent was stripped off and the mixture was heated to 200° for two hours, then cooled and dissolved in benzene. The addition of ether to the benzene solution caused the gradual precipitation of solid from solution. The IR spectrum of the solid, m.p. 108°–109° C., featured characteristic lactone carbonyl and oxazoline (C=N) absorption bands at 5.63 and 6.0 microns, and analyzed for 61.57% C, 8.38% H and 4.69% N. Theory for the adduct (C$_{16}$H$_{27}$O$_5$N) requires 61.32% C, 8.69% H and 4.47% N.

EXAMPLE 37—(OSALAC OXAZOLINE)

Two-tenths mole (73.6 g) of OSALAC described in Example 4 and 0.2 mole (24.2 g) of tris-hydroxymethyl aminomethane (THAM) were added to 100 ml of xylene contained in a reactor equipped with a Dean-Stark moisture trap. The mixture was refluxed fluxed until 5 ml of water were collected (about three hours) and the xylene solvent was then removed by rotoevaporation. The product was diluted in ether and two crops amounting to 71 g were isolated by filtration. The product melted at 121°–122° C. and featured an IR spectrum with prominent lactone carbonyl and oxazoline (C=N) absorption bands. Elemental analyses showed 66.86% C, 10.61H, 3.45% N and 12.01% O. Theory for the osalac oxazoline ($C_{26}H_{47}NO_5$) requires 66.86% C, 10.44% H, 3.09% N and 12.63% O.

EXAMPLE 38—(PIBSALAC OXAZOLINE)

Sixty grams (ca. 0.05 mole) of PIBSALAC described in Example 5 and 6.1 g (0.05 mole) of tris-(hydroxymethyl) aminomethane (THAM) were added to 50 ml of tetrahydrofuran. (THF). The stirred mixture was gradually heated to dissolve the reactants.

The THF solvent was then boiled off, and the reaction temperature was raised to 170° and kept there for about an hour. The residue was dissolved in hexane, filtered and rotoevaporated at 90° C. for four hours, and diluted with an equal weight of neutral oil. The infrared spectrum of the product featured prominent lactone carbonyl and oxazoline (C=N) absorption bands at 5.63 and 6.0 microns.

The diluted product (50% a.i.) showed a hydroxyl number of 43.1 and analyzed for 0.69% nitrogen (by Kjeldahl). The basic nitrogen content, determined by non-aqueous titration with perchloric acid was 0.56%.

EXAMPLE 39—(PIBSALAC OXAZOLINE)

The PIBSALAC prepared in Example 7 and 0.1 mole (12.1 g) of tris-(hydroxylmethyl) aminomethane (THAM) were combined and heated at 180° C. for about four hours. The product was diluted in 200 ml hexane, filtered and rotoevaporated at 90° C. for four hours. The residue was diluted in an equal weight of neutral oil (S-150N). IR analysis of the product showed strong absorption bands at 5.65 and 6.0 microns ascribable to lactone and oxazoline functionality. Analyses revealed that the polyisobutyl lactone oxazoline product contained 0.63% nitrogen by Kjeldahl's method and 0.56% basic nitrogen as determined by non-aqueous titration with perchloric acid. The hydroxyl number of the diluted product (50% a.i.) as determined according to AM-S 240.10-1 was 51.2.

EXAMPLE 40—(HYDROXY-DIBSALAC OXAZOLINE)

Epoxy pibsa (0.01 mole, 2.26 g) described in Example 11 and THAM (0.01, 1.21 g) was dissolved in 10 ml of xylene and refluxed overnight. Removal of the xylene solvent by rotoevaporation gave a concentrate which featured an IR spectrum with the characteristic lactone carbonyl and oxazoline (C=N) absorption bands at 5.70 and 6.01 microns.

EXAMPLE 41—(HYDROXY-PIBSALAC OXAZOLINE)

The hydroxy pibsa lactone acid (ca. 0.05 mole, 130 g of 50% a.i.) described in Example 15 and 0.05 mole (6.05 g) of THAM were mixed and heated to 180° C. for about four hours. The product was diluted in 100 ml hexane, filtered and concentrated by rotoevaporation. The diluted product (50% a.i.) featured an IR spectrum with lactone carbonyl and oxazoline (C=N) absorption bands at 5.7 and 6.03 microns and analyzed for 0.57% nitrogen (Kjeldahl).

EXAMPLE 42—(THIO-BIS-OSALAC OXAZOLINE)

Thio-bis-osalac (0.05 mole, 38.4 g) described in Example 23 and THAM (0.1 mole, 12.1 g) were added to xylene (200 ml) in a reactor fitted with a moisture trap. The mixture was refluxed until about 3 ml of water were collected in the moisture trap (three hours). The hazy xylene solution was filtered, and diluted with acetone to the cloud point. The solids that separated from solution were recovered by filtration. Four crops amounting to 47.5 g were collected. The solid product, m.p. 171°–175° C. featured an IR spectrum with prominent absorption bands at 5.63 and 6.0 microns, and analyzed for 64.95% C., 9.07% H, 3.03% N and 2.92% S. Theory for the thio-bis-lactone oxazoline ($C_{52}H_{92}N_2O_{10}S$) requires 66.63% C, 9.89% H, 3.00% N and 3.42% S. A plausible structure is shown below:

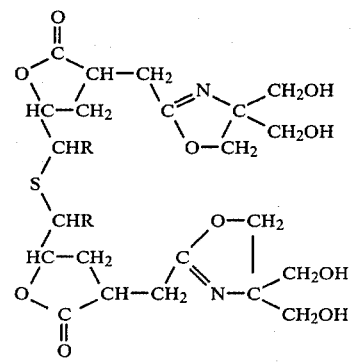

$R = C_{15}H_{31}$

EXAMPLE 43—(THIO-BIS-PIBSALAC OXAZOLINE)

Thio-bis-pibsalac (0.01 mole, 26.3 g) described in Example 26, THAM (0.02 mole, 2.42), and 0.01 g of zinc acetate were added to 26 g of neutral oil (S-150N) and heated to 180° C. for about two hours. The IR spectrum of the product showed absorption bands at 5.65 (lactone) and 6.0 (oxazoline) microns. The diluted product (50% a.i.) analyzed for 0.54% N.

EXAMPLE 44—(CHEMICAL STABILITY OF PIBSALAC OXAZOLINE

Fifteen grams of the product of Example 38 and 1 gram of THAM were combined and heated at 195° C. for six hours. The infrared spectrum of the reaction mixture was virtually identical to that of the PIBSALAC OXAZOLINE reactant indicating that the lactone oxazoline was resistant to further aminolysis by THAM. By way of contrast, treatment of polybutenyl succinic anhydride/mono-THAM ester (formed by reacting polybutenyl succinic anhydride with one mole of THAM at 170° for several hours) with THAM under similar conditions converted the mono-oxazoline ester completely to the bis-oxazoline product in less than an hour.

EXAMPLE 45—THERMAL STABILITY OF PIBSALAC OXAZOLINE

Heating the product of Example 38 at 200° C. for about 20 hours caused no observable changes in its infrared spectrum. Under similar thermolysis conditions, polybutenyl-bis-oxazoline (prepared from polybutenyl succinic anhydride and 2 moles of THAM at 180° for 2 hours) showed distinct changes in its infrared spectrum. Heating caused the dominant absorption band at 6.0 microns (C=N stretching) (characteristic of oxazolines) to gradually diminish and become less intense than the imide-type absorption band (at about 5.85 microns) which eventually dominated the spectrum of the thermalized material after 20 hours.

EXAMPLE 46—SLUDGE INHIBITION BENCH (SIB) TEST

The product of Example 38 and two other dispersant additives were subjected to a Sludge Inhibition Bench (SIB) Test which has been found after a large number of evaluations, to be an excellent test for assessing the dispersing power of lubricating oil dispersant additives.

The medium chosen for the Sludge Inhibition Bench Test was a used crankcase mineral lubricating oil composition having an original viscosity of about 325 SUS at 100° F. that had been used in a taxicab that was driven generally for short trips only, thereby causing a buildup of a high concentration of sludge precursors. The oil that was used contained only a refined base mineral lubricating oil, a viscosity index improver, a pour point depressant and zinc dialkyldithiophosphate antiwear additive. The oil contained no sludge dispersants. A quantity of such used oil was acquired by draining and refilling filling the taxicab crankcase at 1000–2000 mile intervals.

The Sludge Inhibition Bench Test is conducted in the following manner. The aforesaid used crankcase oil, which is milky brown in color, is freed of sludge by centifuging for ½ hour at about 39,000 gravities (gs.). The resulting clear bright red supernatant oil is then decanted from the insoluble sludge particles thereby separated out. However, the supernatant oil still contains oil-soluble sludge precursors which on heating under the conditions employed by this test will tend to form additional oil-insoluble deposits of sludge. The sludge inhibiting properties of the additives being tested are determined by adding to portions of the supernatant used oil, a small amount, such as 0.5, 1.0 or 1.5 weight percent, on an active ingredient basis, of the particular additive being tested. Ten grams of each blend being tested is placed in a stainless steel centrifuge tube and is heated at 280° F. for 16 hours in the presence of air. Following the heating, the tube containing the oil being tested is cooled and then centrifuged for 30 minutes at about 39,000 gs. Any deposits of new sludge that form in this step are separated from the oil by decanting the supernatant oil and then carefully washing the sludge deposits with 15 ml. of pentane to remove all remaining oil from the sludge. Then the weight of the new solid sludge that has been formed in the test, in milligrams, is determined by drying the residue and weighing it. The results are reported as milligrams of sludge per 10 grams of oil, thus measuring differences as small as 1 part per 10,000. The less new sludge formed the more effective is the additive as a sludge dispersant. In other words, if the additive is effective, it will hold at least a portion of the new sludge that forms on heating and oxidation, stably suspended in the oil so it does not precipitate down during the centrifuging.

Using the above described test, the dispersant action of the lactone-oxazoline additives of the present invention was compared with the dispersing power of a commercial dispersant referred to as PIBSA/TEPA. The PIBSA/TEPA was prepared by reaction of 1 mole of tetraethylene pentamine with 1.5 moles of polyisobutenyl succinic anhydride (Sap. No. 80) obtained from polyisobutylene of about 1000 number average molecular weight. The PIBSA/TEPA dispersant was used in the form of an additive concentrate containing about 50 weight percent PIBSA/TEPA in 50 wt. % mineral lubricating oil. This PIBSA/TEPA additive concentrate analyzed about 1.8% nitrogen, indicating that the active ingredient, i.e., PIBSA/TEPA per se, contained about 3.6% nitrogen.

In addition, the lactone-oxazoline product of the present invention was also compared with polyisobutenylsuccinic anhydride-bis oxazoline material prepared in accordance with the teachings of DOS No. 2512201 in the Sludge Inhibition Bench Test. The bis-oxazoline designated PIBSA/Bis THAM dispersant was prepared via the reaction of 2 molar proportions of tris(hydroxymethyl) aminomethane with polyisobutenylsuccinic anhydride according to the procedure, stoichiometry and reaction conditions specified in this patent application. The test results are given in the table below.

TABLE I

| | SLUDGE DISPERSANCY TEST RESULTS | | | |
|---|---|---|---|---|
| | | Mg Sludge/10 g. Oil at | | |
| Additive | % N | 0.5 wt. % | 1.00 wt. % | 1.5 wt. % |
| of Example 38 | 0.69 | 7.70 | 4.37 | 0.0 |
| Blank | | 10.0 | 10.0 | 10.0 |
| PIBSA/BisTHAM | 1.0 | 7.61 | 4.17 | 0.56 |
| PIBSA/TEPA | 1.2 | 7.78 | 3.44 | 2.22 |

The data of Table I illustrates the outstanding dispersant activity of the additive products of the invention when compared a known commercial dispersant referred to as PIBSA-TEPA.

The numerous examples cited above illustrate the novel compositions of the invention and the new processes devised in preparing these compositions; moreover, the examples further illustrate the superb dispersant properties of the polyisobutyl lactone oxazolines and their resistance to oxidation and thermolysis provides a means to exceptionally control lubricant viscosity (manifested by decreased oil thickening) in long drain applications.

The oxidation resistance is illustrated by a test in which air is bubbled through lubricant samples maintained at about 160° C. over a 48-hour period. Each 300 gram sample is modified by the addition of about 5.5 volume percent (50% a.i.) dispersant to measure its respective effect in reducing thickening. 20 parts per million of iron acetylacetonate is added to each sample at the beginning and again at the end of 24 hours. At the end of the test the results were as follows:

| Example | Dispersant Added | Viscosity Poises @ −18° C. |
|---|---|---|
| 1 | none | 46 |
| 2 | Example 38 additive | 68 |
| 3 | PIBSA-TEPA | 80 |

The preparation of the heterosubstituted hydrocarbyl lactone acid materials are produced as noted earlier by reaction with a functionalizing agent of the class consisting of an oxidizing agent or a thiylating agent at a temperature of from −20° C. to 100° C. until functionalization is complete. The preferred oxidizing agent is of the class consisting of peracids, alkyl hydroperoxides and hydrogen peroxide and preferably used when the temperature is from −20° C. to 50° C. The preferred thiylating agents consist of hydrocarbyl sulfenyl halides, a sulfur chloride of the formula $S_xCl_2$ wherein x is an integer of from 1 to 4 and chlorosulfonic acid. The thiylating agents are usefully reacted over the entire range of −20° C. to 100° C., though preferably at from about 20° C. to 80° C.

EXAMPLE 47—SULFO PIBSALAC OXAZOLINE

Seventy grams (0.05 mole) of pibsa (MW ≈960 with a Sap. No. of about 83) were dissolved in 100 ml of tetrahydrofuran (THF) and 6 g. (0.05 g) of chlorosulfonic acid were added dropwise to the stirred THF solution at about 25° C. The addition was exothermic and external cooling was necessary to maintain the reaction temperature at about 25° C. After addition the reaction mixture was stirred at room temperature for an hour, and then 1.0 g of water was added and the mixture was heated at reflux for 2 hours. The THF was stripped off and the residue dissolved in 200 ml. of hexane. The hexane solution was washed twice with 100 ml. of water, dried, and rotoevaporated at 80° C. for 4 hours. The concentrate featured an IR spectrum with strong lactone absorption bands at 5.6–5.71 microns indicating a mixture of 5- and 6- ring lactones, and analyzed for 1.92% sulfur.

Twenty-six grams of the sulfo pibsalac were dissolved in 26 g. of neutral oil, and combined with 5 grams of THAM, and 0.01 g. of $ZnAc_2$. The mixture was heated to 180° C. for about 4 hours, diluted in hexane, filtered and rotoevaporated at 80° C. for 2 hours. Infrared analysis of the product showed the presence of lactone and oxazoline functionality.

The invention in its broader aspects is not limited to the specific details shown and described and departures may be made from such details without departing from the principles of the invention and with sacrificing its chief advantages.

What is claimed is:

1. Thio-bis alkyl lactone acid material selected from the group consisting of carboxylic acid and $C_1$ to $C_{10}$ alcohol ester thereof obtained by a reaction comprising reacting a molar proportion of a hydrocarbon-substituted $C_4$–$C_{10}$ dicarboxylic acid material selected from the group consisting of dicarboxylic acid, ester and anhydrides thereof, or a mixture of said $C_1$ to $C_{10}$ alcohol with said dicarboxylic acid or its anhydride, with about one-half molar proportion of $S_xCl_2$ wherein x is 1 to 4, at a temperature of from −20° C. to 100° C. and evolving HCl in an acid environment to thereby form said thio-bis lactone acid material.

2. A thio-bis alkyl lactone acid material according to claim 1 wherein x is 1.

3. A method for preparing a thio-bis alkyl lactone acid material selected from the group consisting of carboxylic acid and $C_1$ to $C_{10}$ alcohol ester thereof comprising reacting one molar proportion of a hydrocarbon-substituted $C_4$–$C_{10}$ dicarboxylic acid material selected from the group consisting of dicarboxylic acid, $C_1$–$C_{10}$ alcohol ester and anhydrides thereof, or a mixture of said alcohol with said carboxylic acid or its anhydride, with about one-half molar proportion of $S_xCl_2$ wherein x is 1 to 4 at a temperature of from −20° C. to 100° C. and evolving HCl in an acid environment to thereby form said thio-bis alkyl lactone material.

4. A material according to claim 2 wherein said thio-bis alkyl lactone material is oxidized to the sulfoxide and sulfone analogues.

5. A thio-bis alkyl lactone material according to claim 1 wherein said hydrocarbon substituted $C_4$–$C_{10}$ dicarboxylic acid material is alkenyl succinic acid or anhydride having about 8 to 400 carbons in said alkenyl group.

6. A thio-bis alkyl lactone material according to claim 5, wherein said material is said thio-bis alkyl lactone carboxylic acid.

7. A thio-bis alkyl lactone material according to claim 5, wherein said thio-bis alkyl lactone material is said $C_1$ to $C_{10}$ alcohol ester.

8. A thio-bis alkyl lactone material according to claim 5, wherein said alkenyl group is polyisobutenyl of about 900 to 3000 molecular weight.

9. A method according to claim 3 wherein said hydrocarbon substituted $C_4$–$C_{10}$ dicarboxylic acid material is alkenyl succinic acid or anhydride having about 8 to 400 carbons in said alkenyl group.

10. A method according to claim 9, wherein said thio-bis alkyl lactone acid material is said thio-bis alkyl lactone carboxylic acid and said reaction includes adding an acid catalyst to form said acid environment.

11. A method according to claim 9, wherein said thio-bis alkyl lactone material is said ester and said reaction is carried out by reacting said $C_1$ to $C_{10}$ alcohol and said dicarboxylic acid or its anhydride with said $S_xCl_2$, and said acid environment is formed by HCl liberated in the presence of said alcohol.

12. A method according to claim 9, wherein said alkenyl group is polyisobutenyl of about 900 to 3000 molecular weight.

* * * * *